United States Patent

Yoneyama et al.

Patent Number: 5,565,435
Date of Patent: Oct. 15, 1996

[54] α-GLYCOSYL QUERCETIN, AND ITS PREPARATION AND USES

[75] Inventors: Masaru Yoneyama; Satoshi Iritani; Toshio Miyake, all of Okayama, Japan

[73] Assignee: Kabushiki Kaisha Hayashibara Seibutsu Kagaku Kenkyujo, Okayama, Japan

[21] Appl. No.: 390,277

[22] Filed: Feb. 15, 1995

Related U.S. Application Data

[63] Continuation of Ser. No. 918,745, Jan. 27, 1992, abandoned.

[30] Foreign Application Priority Data

Jul. 26, 1991 [JP] Japan .................. 3-208709

[51] Int. Cl.$^6$ .......................... A61K 31/70; C07H 15/24; C12P 19/18; C12P 19/14
[52] U.S. Cl. ................. 514/27; 536/8; 536/124; 435/75; 435/96; 435/97; 435/99
[58] Field of Search ................... 536/8, 124; 435/99, 435/97, 75, 96; 514/27

[56] References Cited

U.S. PATENT DOCUMENTS

| | | | |
|---|---|---|---|
| 3,888,842 | 6/1975 | Cazaux et al. | 536/8 |
| 5,122,381 | 6/1992 | Nishimura et al. | 426/654 |
| 5,145,781 | 9/1992 | Suzuki et al. | 536/8 |

FOREIGN PATENT DOCUMENTS

| | | | |
|---|---|---|---|
| 0420376 | 3/1990 | European Pat. Off. | C07H 17/07 |
| 0387042 | 3/1990 | European Pat. Off. | C12P 19/60 |
| 4312597 | 4/1992 | Japan | A23D 9/00 |

OTHER PUBLICATIONS

Chemical Abstracts, vol. 99, Oct. 10, 1983. p. 380, abstract No. 119306p.
Chemical Abstracts, vol. 76, Mar. 13, 1972, p. 500, abstract No. 59958r.
Chemical Abstracts, vol. 75, Nov. 22, 1971, p. 32, abstract No. 126531r.
Chemical Abstracts, vol. 87, Sep. 26, 1977 p. 350, abstract No. 98984t.
Fragrance Journal 83, pp. 36–39, (1987); "Analysis of propolis and its quality evaluation".
Natural Therapeutics "Propolis", 2nd revised edition; by Dr. Yves Donadieu, 1983.

*Primary Examiner*—John W. Rollins
*Assistant Examiner*—Francisco C. Prats
*Attorney, Agent, or Firm*—Browdy and Neimark

[57] ABSTRACT

A novel α-glycosyl quercetin, wherein at least equimolar D-glucose residues are attached to quercetin via the α-bond, has a satisfactory water-solubility, light tolerance and stability, and exerts the inherent activity of quercetin in vivo. The α-glycosyl quercetin is prepared by a process comprising subjecting a solution containing quercetin and an α-glucosyl saccharide to the action of a saccharide-transferring enzyme to form an α-glycosyl quercetin, and recoverying the resultant α-glycosyl quercetin. The α-glycosyl quercetin can be advantageously used in combination with other materials in food products, cosmetic compositions and pharmaceutical compositions as a highly-safe and natural vitamin P-enriched agent, yellow-color-imparting agent, antioxidant, deodorant, stabilizer, quality-improving agent, antiseptic, prophylactic agent, therapeutic agent and ultraviolet-absorbing agent.

12 Claims, 2 Drawing Sheets

５,565,435

α-GLYCOSYL QUERCETIN, AND ITS PREPARATION AND USES

This application is a continuation of application Ser. No. 07/918,745, filed Jan. 27, 1992 now abandoned.

BACKGROUND OF THE INVENTION

1. Field of the Invention

The present invention relates to a novel α-glycosyl quercetin, and its preparation and uses, more particularly, it relates to (i) an α-glycosyl quercetin wherein at least equimolar D-glucose residues are attached to quercetin via the α-bond; (ii) a process for preparing α-glycosyl quercetin comprising subjecting a solution containing quercetin and an α-glucosyl saccharide to the action of a saccharide-transferring enzyme to form an α-glycosyl quercetin; and recovering the resultant α-glycosyl quercetin, and (iii) a composition, for example, food products, cosmetics and pharmaceuticals for susceptive diseases, into which said α-glycosyl quercetin is incorporated.

2. Description of the Prior Art

Usually, quercetin is widely distributed in the plant kingdom as a glycoside, i.e. rutin wherein a saccharide is attached to quercetin via the β-bond, and can be prepared by extracting and separating such a glycoside from plants and hydrolyzing the resultant glycoside with an acid or an enzyme to remove saccharides therefrom.

Quercetin has a relatively-large resonance structure in terms of the chemical structure, and this exhibits a yellow-color-imparting ability, antioxidation activity, vitamin-P activity and ultraviolet-absorbing activity. Thus, quercetin could be useful in the fields of food products, pharmaceuticals and cosmetics.

Quercetin, however, is soluble in a readily water-soluble organic solvent, but insoluble or scarcely soluble in water, and this renders the handleability very difficult.

Propolis is an example of the fact that a large amount of quercetin is present in the natural world. As described in *Propolis in natural therapeutics* (1983), published by Maloine Editeur S. A., Paris, France, and *Fragrance Journal*, No. 83, pp. 36–39 (1987), propolis is a resin-like product which is stored by bees in a beehive, said propolis containing resins, beeswaxes, essential oils, pollens and flavonoids, and has been used in a variety of folk medicines for a long time.

Recently, it was found that flavonoids in propolis were mainly composed of flavon aglycons such as chrysin, and flavonol aglycons such as galangin and quercetin, said flavonoids having been noticed as a major effective component of propolis.

The flavonoids are prepared by the extraction of propolis with a readily water-soluble organic solvent such as methanol and ethanol, and an extract prepared in this manner has been commercially available in these days as a propolis extract or a propolis tincture.

The flavonoids, however, dissolve in a water-soluble organic solvent, but are insoluble or scarcely soluble in water, and this strongly restricts their actual use.

SUMMARY OF THE INVENTION

There has been a great demand to overcome conventional drawbacks of quercetin and to realize a quercetin derivative which has a satisfactory water-solubility and which exerts a satisfactory physiological-activity in vivo without fear of causing side effects.

The present invention was made to overcome the above drawbacks, more particularly, the present inventors studied to obtain a novel quercetin derivative by using a biochemical technique.

As a result, the present inventors found that a novel α-glycosyl quercetin having a satisfactory water-solubility, as well as being readily hydrolyzed in vivo to exert the inherent physiological activity of quercetin without fear of causing side effects, was formed by subjecting a solution containing quercetin and an α-glucosyl saccharide to the action of a saccharide-transferring enzyme, and the preparation of the α-glycosyl quercetin and its uses in food products, cosmetics and pharmaceuticals for the prevention and/or the treatment of susceptive diseases was established. This α-glycosyl quercetin is not hydrolyzed by β-glucosidase. Thus, the present inventors accomplished this invention.

The present inventors also found that an α-glycosyl quercetin formed by a saccharide-transferring reaction and which is not hydrolyzed by β-glucosidase was readily purified by allowing a post-reaction solution to contact a synthetic macroporous resin wherein the difference of adsorbing ability of substances on the resin was utilized.

The preparation of the present α-glycosyl quercetin which is not hydrolyzed by β-glucosidase overcomes all conventional drawbacks in the prior art and strongly facilitates the realization of an industrial-scale preparation of an α-glycosyl quercetin.

BRIEF DESCRIPTION OF THE ACCOMPANYING DRAWINGS

DETAILED DESCRIPTION OF THE INVENTION

Figure 1:
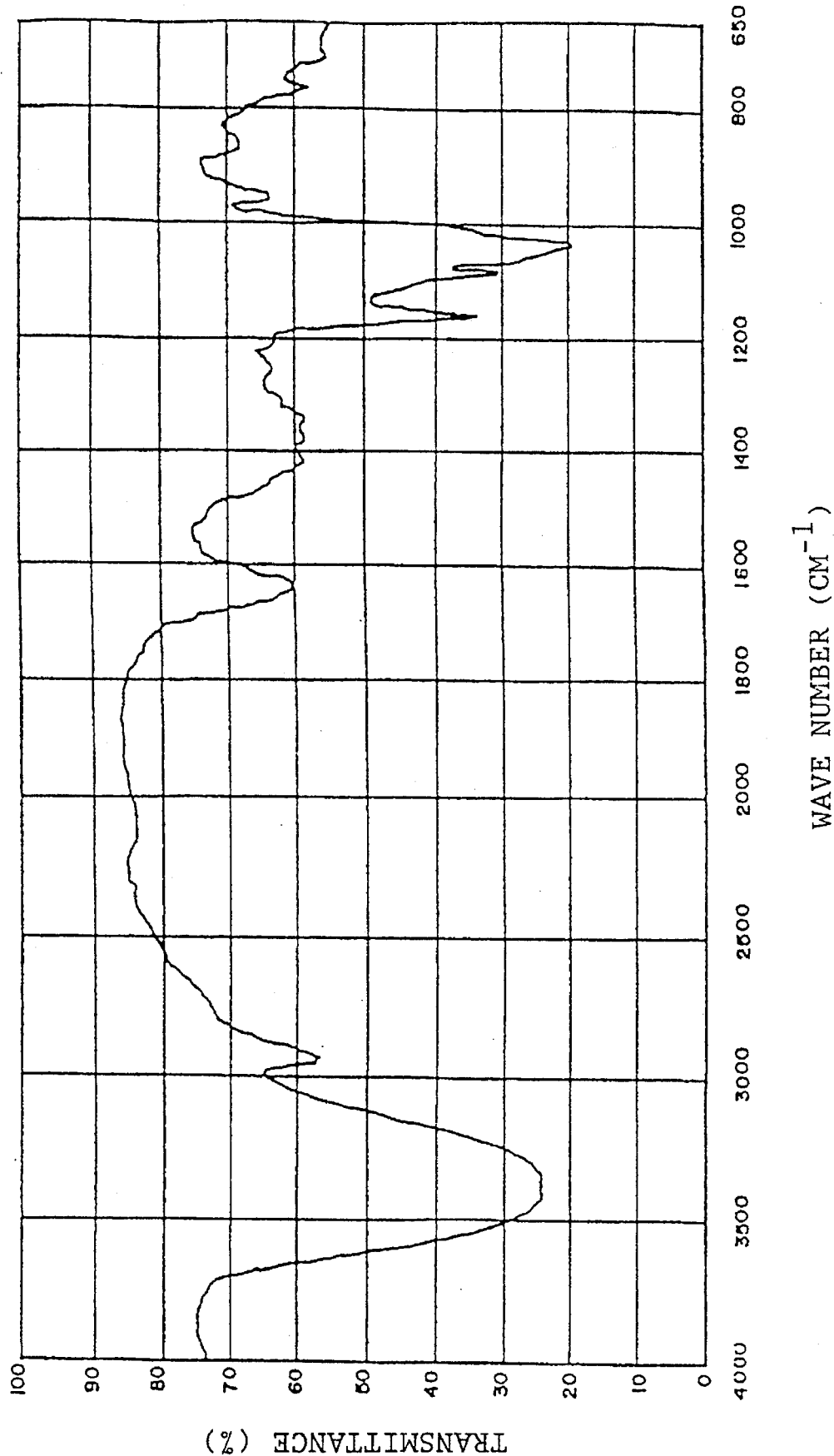
FIG.1 shows the infrared absorption spectrum of the present α-glycosyl quercetin specimen [II].

The quercetin usable in the invention includes both a quercetin specimen prepared by the hydrolysis of rutin and a mixture of quercetin and flavonoids, e.g. propolis.

The quercetin prepared from propolis suitably usable in the invention includes a highly-purified quercetin, as well as an extract extracted from propolis with a readily water-soluble organic solvent or a partially-purified product prepared by dewaxing the extract, a suspension boiled out of propolis, and an extract extracted from propolis with an alkaline solution. If necessary, commercially-available quercetin products and those obtained by a chemical synthesis can be favorably used in the invention.

The α-glucosyl saccharides which can be used in the present invention are those which can be utilized for the formation of an α-glycosyl quercetin by a saccharide-transferring enzyme. For example, partial starch hydrolysates such as amylose, dextrins, cyclodextrins and maltooligosaccharides, as well as a liquefied- or gelatinized-starch, can be suitably chosen.

A specific α-glucosyl saccharide suitable for a saccharide-transferring enzyme is chosen in order to facilitate the formation of an α-glycosyl quercetin.

In case of using α-glucosidase (EC 3.2.1.20) as a saccharide-transferring enzyme, maltooligosaccharides such as maltose, maltotriose and maltotetraose, as well as partial starch hydrolysates having a dextrose equivalent (DE) of about 10–70, can be favorably used as an α-glucosyl saccharide; in case of using cyclomaltodextrin glucanotransferase (EC 2.4.1.19), cyclodextrins or amylaceous substances having a DE of about 60 or lower, i.e. gelatinized starch having a DE of one or lower and partial starch hydrolysates having a DE of about 60, can be favorably used; and in case of using α-amylase (EC 3.2.1.1), amylaceous substances having a DE of about 30 or lower, i.e. gelatinized starch having a DE of one or lower and dextrins or partial starch hydrolysates having a DE of about 30, can be favorably used.

The concentration of an α-glucosyl saccharide suitable for an enzymatic reaction is about 0.5–100-fold, preferably, about 2–20-fold of that of quercetin.

The quercetin-containing solutions suitable for an enzymatic reaction are those which contain the possible highest level of quercetin, for example, those having a relatively-high concentration of quercetin in the form of suspension or solution which is prepared by dissolving quercetin in the presence of an organic solvent or under a relatively-high temperature condition or under an alkaline condition exceeding pH 7.0, said solutions having a concentration of about 0.01 w/v % or higher, preferably, about 0.1–10.0 w/v % of quercetin.

The saccharide-transferring enzymes usable in the invention include those which can form an α-glycosyl quercetin without decomposing quercetin when allowed to act on a solution containing quercetin and an α-glucosyl saccharide having a suitable property for the enzymes.

Examples of such a saccharide-transferring enzyme appropriately used in the invention are α-glucosidases derived from animal and plant tissues such as pig liver and buckwheat seed, and from a culture obtainable by cultivating in a nutrient culture medium microorganisms including bacteria, molds and yeasts such as those of the genera Mucor, Penicillium and Saccharomyces; cyclomaltodextrin glucanotransferases derived from a culture of bacteria such as those of the genera Bacillus and Klebsiella; and α-amylases derived from a culture of fungi such as those of the genus Aspergillus.

The saccharide-transferring enzymes should not necessarily be purified prior to use as long as they fulfill the above requirements, and, usually crude saccharide-transferring enzymes can attain the object of the invention.

If necessary, the saccharide-transferring enzymes can be purified by conventional methods, prior to use. Furthermore, commercially-available saccharide-transferring enzymes can be used in the invention.

The amount of a saccharide-transferring enzyme and a reaction time are closely depended on each other. From an economical viewpoint, a saccharide-transferring enzyme is usually used in an amount of which completes an enzymatic reaction within about 5–80 hours.

Immobilized saccharide-transferring enzymes can be appropriately used batchwise and in a continuous manner.

it is recommendable to effect an enzymatic reaction under a light-shielded condition as much as possible in order to prevent the decomposition of quercetin in a reaction solution.

A post-reaction solution containing an α-glycosyl quercetin obtained in this manner can be used intact as a product containing an α-glycosyl quercetin without any further treatment. Usually, a post-reaction solution is filtered and concentrated into an α-glycosyl quercetin syrup which is then dried and pulverized into an α-glycosyl quercetin powder, if necessary.

The product thus obtained can be advantageously used as a vitamin P-enriched agent, as well as a highly-safe and natural yellow-color-imparting agent, antioxidant, deodorant, stabilizer, quality-improving agent, antiseptic, prophylactic agent, therapeutic agent and ultraviolet-absorbing agent, in combination with other materials in food products, cigarettes, tobaccos, feeds, pet foods, agents for susceptive diseases, cosmetics and plastics.

In case of preparing a purified α-glycosyl quercetin product, it can be prepared by separating an α-glycosyl quercetin from a crude α-glycosyl quercetin containing concomitants such as α-glucosyl saccharides with a synthetic macroporous resin wherein the difference of adsorbing ability of substances on the resin is utilized.

The wording "synthetic macroporous resin" as referred to in the invention means non-ionic and porous synthetic-resins which have a relatively-large adsorptive area such as a styrene divinyl benzene copolymer, phenol-formaldehyde resin, acrylic resin and methacrylate resin. Examples of such a resin are "Amberlite XAD-1", "Amberlite XAD-2", "Amberlite XAD-4", "Amberlite XAD-7", "Amberlite XAD-8", "Amberlite XAD-11" and "Amberlite XAD-12", products of Rohm & Haas Company, Philadelphia, USA; "Diaion HP-10", "Diaion HP-20", "Diaion HP-30", "Diaion HP-40" and "Diaion HP-50", products of Mitsubishi Chemical Industries Ltd., Tokyo, Japan; and "Imac Syn-42", "Imac Syn-44" and "Imac Syn-46" products of Industri de Maatshappily activate N.V., Amsterdam, Netherlands.

The purification method of a post-reaction solution containing the present α-glycosyl quercetin is effected by feeding the solution to a column packed with a synthetic macroporous resin, whereby the α-glycosyl quercetin and intact quercetin are adsorbed on the resin, while a large amount of concomitant α-glucosyl saccharides and water-soluble saccharides are eluted from the column without adsorbing on the resin.

After completion of an enzymatic reaction, two or more purification methods such as filtration to remove insoluble substances formed in a reaction solution by neutralizing or heating the solution; adsorption to remove proteinaceous substances formed in a reaction solution by treating the solution with magnesium alumino silicate or magnesium aluminate; and deionization using ion-exchange resin (H- and OH-forms) can be advantageously used in combination before contacting a post-reaction solution to a synthetic macroporous resin, if necessary.

The α-glycosyl quercetin and intact quercetin, which have been selectively adsorbed on a synthetic macroporous resin in a column, are first washed with a solution such as water, then the column is fed with a solution such as aqueous methanol- and ethanol-solutions, followed by the elution of the α-glycosyl quercetin. Thereafter, intact quercetin adsorbed on the resin is eluted from the column with an increase of the volume of the eluate or the concentration of the organic solvent.

A syrup containing an α-glycosyl quercetin as a main component can be obtained by distilling a high-α-glycosyl quercetin content solution to remove an organic solvent and concentrating the resultant solution to give a prescribed concentration. A powder containing an α-glycosyl quercetin as a main component can be prepared by drying and pulverizing the syrup.

The elution step of the α-glycosyl quercetin and intact quercetin with an organic solvent enables the regeneration and the repeated use of a synthetic macroporous resin.

The present purification step with a synthetic macroporous resin has an advantageous feature in that it can simultaneously remove concomitants such as α-glucosyl saccharides, water-soluble saccharides and water-soluble salts. The α-glycosyl quercetin thus obtained has the following features:

(1) It has a higher level of water-solubility by a large margin than intact quercetin;

(2) It has a higher level of light tolerance and stability than intact quercetin;

(3) It exhibits substantially the same- or a slightly-lower level of yellow-color-imparting ability than intact quercetin;

(4) It is hydrolyzed by the in vivo enzyme into quercetin and glucose to exert the inherent physiological activity of quercetin (vitamin P activity). When it is used in combination with vitamin C, the physiological activity is more augmented; and (5) When it contains an α-glucosyl saccharide, it exerts the inherent activity of α-glycosyl quercetin, and the α-glucosyl saccharides act as a filler, diluent or sweetener. When it is a purified product free of α-glucosyl saccharides, the product exerts the inherent activity of α-glycosyl quercetin without substantially acting as a filler or diluent.

These features render the present α-glycosyl quercetin advantageously usable as a highly-safe and natural vitamin P-enriched agent, yellow-color-imparting agent, antioxidant, deodorant, stabilizer, quality-improving agent, antiseptic, prophylactic agent, therapeutic agent, and ultraviolet-absorbing agent, in combination with other materials in food products, cigarettes, tobaccos, feeds, pet foods, agents for susceptive diseases, plastics and cosmetics such as skin-refining agents and skin-whitening agents.

More particularly, the vitamin-P activity of the present α-glycosyl quercetin can be advantageously more augmented by combining it with one or more derivatives of flavonoid saccharides such as rutin, hesperidin and naringin which have been recently paid attention as a bioflavonoid, as well as their α-glycosyl saccharide derivatives.

The taste of the present α-glycosyl quercetin well harmonizes with other substances having a sour, saltiness, astringency, bitterness or deliciousness, and has a satisfiable acid-tolerance and thermal resistance, and these render the α-glycosyl quercetin advantageously useful in general food products, cigarettes and tobaccos such as seasonings, Japanese-style confectoneries, western-style confectoneries, ice creams, sherbets, beverages, spreads, pastes, pickled products, canned products, processed marine products, processed meat and fish meat products, processed milk and egg products, processed vegetable products, processed fruit products and processed cereal products. The α-glycosyl quercetin can be advantageously used to improve its taste and flavor in combination with one or more sweeteners, for example, those from plants such as stevioside, α-glycosyl stevioside, rebaudioside A, glycyrrhizin, α-glycosyl glycyrrhizin and dihydrochalcone; those of amino acids such as glycine, alanine and L-aspartyl-L-phenylalanine methyl ester; and those of saccharides such as sucrose, partial starch hydrolysate (thick malt syrup), glycosyl sucrose, glucose, isomerised sugar, fructose, honey, maltose, sorbitol, maltitol and lactose. The α-glycosyl quercetin prevents the crystalization and sedimentation of flavonoids present in a fruit juice, and this renders it advantageously useful as a turbidity- or dim-preventing agent for beverages and jellies containing a fruit juice. The α-glycosyl quercetin can be also advantageously used in feeds and pet foods for domestic animals, bees, silkworms and pet fishes as a vitamin P-enriched agent or a taste-improving agent.

Furthermore, the α-glycosyl quercetin can be advantageously used in cigarettes, tobaccos, pharmaceuticals and cosmetics in the form of solid, paste and liquid, for example, troche, cod-liver oil, complex vitamin, sublingual tablet, cachou, oral refrigerant, gargle, intubation nutrition, crude drug, dentifrice, internal medicine, injection, lipstick, lip cream, sun-screening, prophylactic and/or therapeutic-agent for susceptive diseases, skin-refining agent, skin-whitening agent and hair-restorer. In addition, the α-glycosyl quercetin can be used in plastics as an ultraviolet-absorbing agent and deterioration-preventing agent.

The wording "susceptive diseases" as referred to in the invention means those which can be prevented and/or treated with the present α-glycosyl quercetin. Examples of such susceptive diseases are viral diseases, bacterial diseases, traumatic diseases, immunopathies, rheumatisms, diabetes, diseases of circulatory organs, malignant tumors and nervous diseases. The form of such a prophylactic and/or therapeutic agent for susceptive diseases can be freely chosen to meet to its final use. Examples of such a form are liquid agents such as nebula, collyrium, collunarium, gargle and injection; agents in the form of a paste such as ointment, cataplasm and cream; and agents in the form of a solid such as powder, granule, capsule and tablet. In the preparation of these agents, the present α-glycosyl quercetin can be suitably used in combination with one or more other substances such as therapeutic agents, biologically active substances, antibiotics, adjuvants, fillers, stabilizers, color-imparting agents and flavor-imparting agents, if necessary.

The dose of the prophylactic and/or therapeutic agents for susceptive diseases can be adequately controlled dependently on the content of the present α-glycosyl quercetin in the agents and their administration route and frequency. Usually, a dose in the range of about 0.001–10.0 g/day/adult of α-glycosyl quercetin, on the dry solid basis (d.s.b.), is favorably used.

In case of cosmetics, the present α-glycosyl quercetin can be used similarly as in the case of the above-mentioned agents.

The α-glycosyl quercetin can be advantageously incorporated into a product before the completion of the processing by using conventional methods, for example, mixing, kneading, dissolving, soaking, penetrating, dispersing, applying, spraying and injecting.

The following experiments will explain the present α-glycosyl quercetin in detail.

EXPERIMENT 1

Preparation of α-Glycosyl Quercetin

EXPERIMENT 1-(1)

Saccharide-Transferring Reaction

One part by weight of quercetin and 6 parts by weight of dextrin (DE 20) were added with 500 parts by weight of water, and the mixture was adjusted to pH 9.5 and dissolved by heating under an anaerobic condition. Thereafter, the resultant mixture was cooled to 60° C., added with 40 units per g dextrin of a cyclomaltodextrin glucanotransferase specimen from *Bacillus stearothermophilus*, commercialized by Hayashibara Biochemical Laboratories, Inc, Okayama, Japan, and subjected to an enzymatic reaction at pH 8.5 or higher and at 60° C. for 18 hours. After completion of the enzymatic reaction, the reaction solution was heated to inactivate the remaining enzyme to obtain a solution containing an α-glycosyl quercetin.

EXPERIMENT 1-(2)

Purification

A post-reaction solution obtained by the method in Experiment 1-(1) was filtered and neutralized, and the resultant solution was fed at a flow rate of SV 2 to a column packed with "Diaion HP-10", a synthetic macroporous resin, commercialized by Mitsubishi Chemical Industries Ltd., Tokyo, Japan. The column was first washed with water, then fed with 50 v/v % ethanol, and the effluent was concentrated to remove ethanol and pulverized to obtain a yellow-colored α-glycosyl quercetin specimen [I] in the yield of about 220% against the weight of the material quercetin, d.s.b.

EXPERIMENT 1-(3)

Hydrolysis by Amylase

An α-glycosyl quercetin specimen [I] prepared by the method in Experiment 1-(2) was dissolved in water into a 1 w/v % solution which was then added with 100 units per g specimen [I] of glucoamylse (EC 3.2.1.3), commercialized by Seikagaku-Kogyo Co., Ltd., Tokyo, Japan, and subjected to an enzymatic reaction for 5 hours while keeping the pH and temperature at 5.0° and 55° C. The reaction solution was heated to inactivate the remaining enzyme and fed at a flow rate of SV 2 to a column packed with "Diaion HP-10", a synthetic macroporous resin, commercialized by Mitsubishi Chemical Industries Ltd., Tokyo, Japan. As a result, an α-glycosyl quercetin and intact quercetin in the reaction solution were adsorbed on the resin, while glucose and salts were eluted from the column without adsorbing on the resin. Thereafter, the column was washed with water and fed with an aqueous ethanol solution while increasing the concentration of ethanol stepwise to effect fractionation, followed by recovering an α-glycosyl quercetin fraction. The resultant fraction was concentrated and pulverized to obtain a yellow-colored α-glycosyl quercetin specimen [II] in the yield of about 50% against the weight of the material quercetin, d.s.b.

EXPERIMENT 2

Physicochemical Properties of α-Glycosyl Quercetin (1) Solubility in solvent It is readily soluble in water and 0.1N sodium hydroxide; slightly soluble in methanol and ethanol; and insoluble in ether, benzene and chloroform. The solubility of the α-glycosyl quercetin specimen [I] in 25° C. water (pH 7) is about 10 w/v %, while that of intact quercetin is about 0.0002 w/v %.

(2) Taste

Intact quercetin and the α-glycosyl quercetin specimens [I] and [II] were respectively kept in the mouth directly and their tastes were compared. It was revealed that intact quercetin was tasteless as if you bite a grain of sand because intact quercetin did not melt in the mouth, while both of the specimens [I] and [II] smoothly melted in the mouth and exhibited a mild sweetness.

(3) Ultraviolet-absorption spectrum

In order to compare the α-glycosyl quercetin specimen [I] or [II] with intact quercetin, their ultraviolet-absorption spectra were measured with methanol solution. The specimens [I] and [II] similarly as intact quercetin exhibited the first and the second maximum absorption peaks near 253 nm and 373 nm respectively.

(4) Infrared-absorption spectrum

Figure 2:
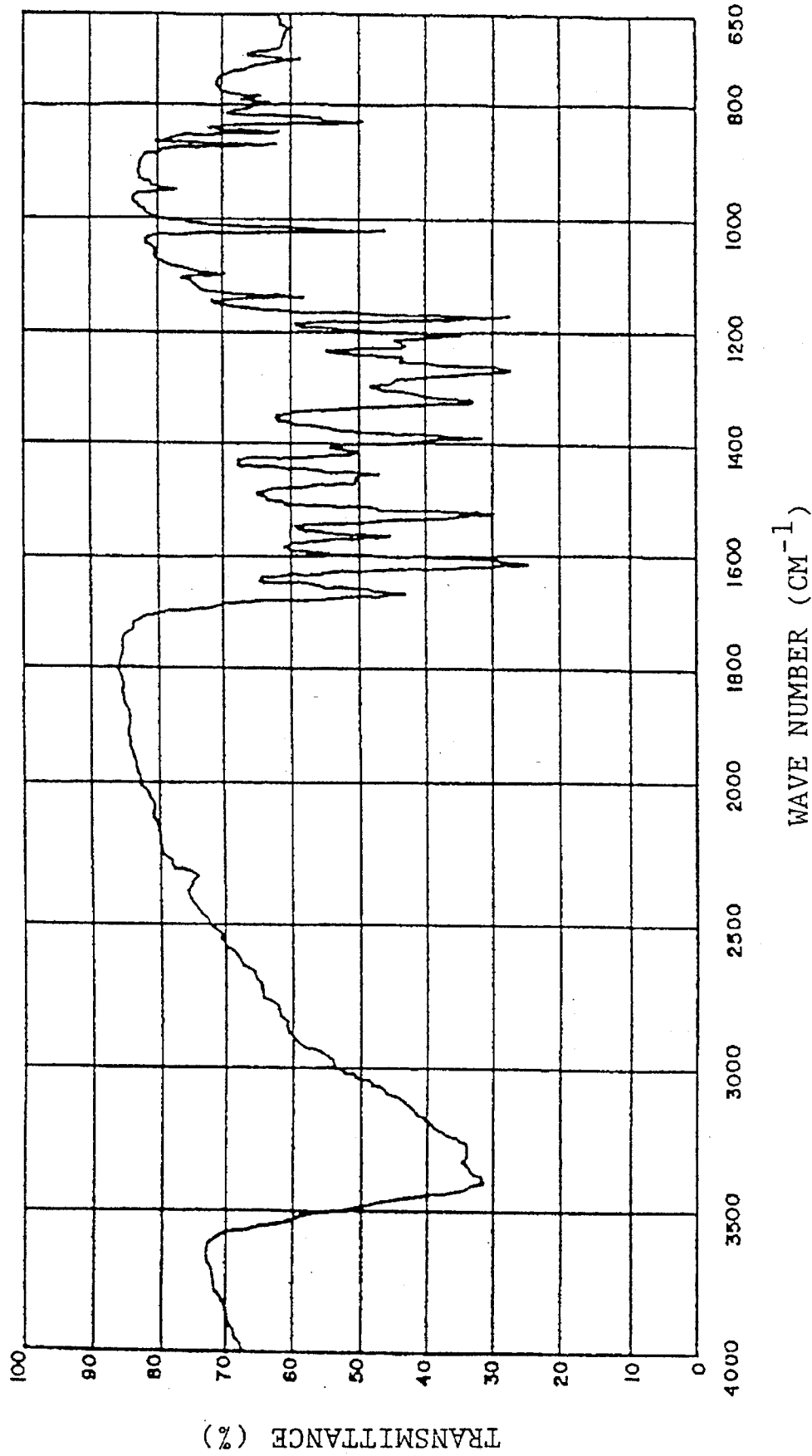
FIG.2 shows the infrared absorption spectrum of intact quercetin as a control.

By using the KBr tablet method, the infrared-absorption spectrum of the α-glycosyl quercetin specimen [II] was studied. FIG.1 shows the result of the α-glycosyl quercetin specimen [II]. FIG. 2 shows the result of intact quercetin as a control.

(5) Stability on hydrolysis (a) The α-glycosyl quercetin specimens are hydrolyzed by α-glucosidase (EC 3.2.1.20) from pig liver to form quercetin and D-glucose.

(b) The α-glycosyl quercetin specimens are hydrolyzed by β-glucosidase.

(6) Analysis on high-performance liquid chromatography (HPLC)

(a) Method of analysis

Apparatus : WATERS MODEL M-6000A, a pump system commercialized by Japan Waters Ltd., Tokyo, Japan;

Column: ODS-M column, a column product commercialized by Shimadzu Techno-Research, Inc., Kyoto, Japan;

Column temperature : 53° C.;

Eluate : water:methanol : acetic acid =60:30:1

Flow rate : 0.5 ml/min; and

Detection wave length : at 255 nm.

(b) Result

As a result, the specimen [I] exhibited the inherent peak of quercetin at a retention time of 62 min and exhibited new peaks at 54, 44, 38, 33, 30, 26, 25, 23, 21 and 19 min, while the specimen [II] exhibited two relatively-large peaks at 54 and 38 min in addition to a small peak corresponding to the inherent peak of quercetin at 62 min.

Based on the results, a substance exhibiting new peaks contained in the specimen [I] was determined as an α-glycosyl quercetin wherein equimolar or more D-glucose residues are attached to quercetin via the α-bond.

Two substances exhibiting new peaks contained in the specimen [II] were determined as α-glycosyl quercetins wherein equimolar or more D-glucose residues are attached to different positions of quercetin skeleton. As described above, the α-glycosyl quercetin according to the present invention is a novel saccharide derivative of quercetin having a satisfactory water-solubility wherein equimolar or more D-glucose residues are attached to quercetin via the α-bond. The α-glycosyl quercetin is readily hydrolyzed by α-glucosidase to exert the inherent physiological activity of quercetin when administered to a living body.

(7) Antioxidation activity

Ten ml of about one % linoleic acid in ethanol solution, 10 ml of 50 mM phosphate buffer and 5 ml water were mixed, and 5 ml aliquots of the mixture were distributed to 5 ml-flasks. Each flask was added with the α-glycosyl quercetin specimen [I] or [II] to give a concentration of 200 ppm, sealed, and allowed to stand at 50° C. under a light-shielded condition. As a control, dl-α-tocopherol which had been used as a typical antioxidant was used. A half ml of solution was sampled from each flask at a prescribed time interval, and the sampled solution was subjected to high-performance liquid chromatography (HPLC) to analyze the amount of hydroperoxide which was formed as a result of the oxidation of linoleic acid. The conditions used in the analysis of hydroperoxide were as follows:

Apparatus : WATERS MODEL M-6000A, a pump system commercialized by Japan Waters Ltd., Tokyo, Japan;
Column : ODS-M column, a column commercialized by Shimadzu Techno-Research, Inc., Kyoto, Japan;
Column temperature : 35° C.
Eluate : water:methanol:acetic acid =75:25:0.1
Flow rate : 0.5 ml/min
Detection wave length: at 235 nm
The results were as shown in Table 1.

TABLE 1

Antioxidation activity

| Sample | Sampling day | | | |
|---|---|---|---|---|
| | 0 | 4 | 7 | 8 |
| Control | 0.3 | 1.5 | 5.3 | 7.1 |
| Added with dl-α-Tocopherol | 0.3 | 1.1 | 4.5 | 6.0 |
| Added with α-Glycosyl quercetin specimen [I] | 0.3 | 0.7 | 3.9 | 5.1 |
| Added with α-Glycosyl quercetin specimen [II] | 0.3 | 0.6 | 3.7 | 4.8 |

Note: Each value indicates a relative intensity determined with the peak area corresponding to hydroperoxide.

Based on the results in Table 1, the α-glycosyl quercetin specimens [I] and [II] exhibited a higher antioxidation activity than dl-α-tocopherol.

EXPERIMENT 3

Acute Toxicity

An α-glycosyl quercetin specimen [I] prepared by the method in Experiment 1-(2) was tested on the acute toxicity by using 7 week-old dd mice. As a result, no mouse died up to a dose of 5 g of the specimen and a higher dose test was impossible.

Thus, the acute toxicity of the specimen is extremely low. Similarly as above, an α-glycosyl quercetin specimen [II] prepared by the method in Experiment 1-(3) was tested on the acute toxicity to obtain the same result as in the specimen [I]. Thus, it was revealed that the acute toxicity of the specimen [II] was also extremely low.

The preparations and uses of the present α-glycosyl quercetin will be described in the following Examples A and B.

EXAMPLE A-1

α-Glycosyl Quercetin

To 200 parts by weight of water was added one part by weight of quercetin and 4 parts by weight of dextrin (DE 10), and the suspension was adjusted to pH 9.8, dissolved by heating under an anaerobic condition, cooled to 60° C., immediately added with 40 units per g dextrin of a cyclomaltodextrin glucanotransferase specimen from *Bacillus stearothermophilus*, commercialized by Hayashibara Biochemical Laboratories Inc., Okayama, Japan, and subjected to an enzymatic reaction at pH 8.5 or higher and at 55° C. for 24 hours under anaerobic- and stirring-conditions. HPLC analysis of the reaction solution revealed that about 50% quercetin converted into α-glycosyl quercetins such as α-glucosyl quercetin, α-maltosyl quercetin and α-maltotriosyl quercetin. The reaction solution was neutralized, heated to inactivate the remaining enzyme and filtered, and the filtrate was in the usual manner deionized and purified by using an ion-exchange resin (H- and OH-forms), and concentrated to obtain an α-glycosyl quercetin syrup containing an α-glucosyl saccharide in the yield of about 80% against the weight of the material, d.s.b.

The product can be advantageously used in combination with other materials in food products, cigarettes, tobaccos, feeds, pet foods, agents for susceptive diseases, cosmetics and plastics as a vitamin p-enriched agent with an improved water-solubility, as well as a highly-safe and natural yellow-color-imparting agent, antioxidant, stabilizer, quality-improving agent, prophylactic agents, therapeutic agents and ultraviolet-absorbing agents.

EXAMPLE A-2

α-Glucosyl Quercetin

One part by weight of an α-glycosyl quercetin syrup containing an α-glucosyl saccharide, prepared in accordance with the method in Example A-1, was dissolved in 4 parts by weight of water, added with 100 units per g α-glycosyl quercetin of glucoamylase (EC 3.2.1.3), commercialized by Seikagaku-Kogyo Co., Ltd., Tokyo, Japan, and subjected to an enzymatic reaction at 50° C. for 5 hours. HPLC analysis of the reaction solution revealed that the α-glycosyl quercetin was converted into two types of α-glucosyl quercetin wherein a D-glucose residue is attached to a different position of quercetin moiety. The reaction solution was heated to inactivate the remaining enzyme and fed at a flow rate of SV 2 to a column packed with "Diaion HP-10", a synthetic macroporous resin commercialized by Mitsubishi Chemical Industries Ltd., Tokyo, Japan. As a result, the α-glucosyl quercetins and intact quercetin in the reaction solution adsorbed on the resin, while glucose and salts were eluted from the column without adsorbing on the resin. Thereafter, the column was first washed with water, then fed with aqueous ethanol solution while increasing the concentration of ethanol stepwise to fractionate the α-glucosyl quercetins. The resultant fraction containing α-glucosyl quercetins was concentrated in vacuo and pulverized to obtain an α-glucosyl quercetin powder in the yield of about 50% against the weight of the material quercetin, d.s.b.

It was revealed that one mole of D-glucose was formed per mole of quercetin when the α-glucosyl quercetins were hydrolyzed with an acid, and the α-glucosyl quercetins were hydrolyzed into quercetin and D-glucose when subjected to the action of a partially-purified α-glucosidase specimen which had been extracted from pig liver and partially purified.

The product can be advantageously used in combination with other materials in food products, cigarettes, tobaccos, agents for susceptive diseases, cosmetics and plastics, as a highly-purified vitamin p-enriched agent with an improved water-solubility, as well as a yellow-color-imparting agent, antioxidant, stabilizer, quality-improving agent, prophylactic agents, therapeutic agents and ultraviolet-absorbing agents.

EXAMPLE A-3

Mixture of α-Glycosyl Quercetin and Flavonoid

One part by weight of a flavonoid mixture containing chrysin, galangin and quercetin, which had been prepared in conventional manner by dewaxing a propolis extract extracted with ethanol, and 10 parts by weight of dextrin (DE 8) were added with 200 parts by weight of water, and the suspension was adjusted to pH 9.8, dissolved by heating under an anaerobic condition, cooled to 60° C., added with 50 units per g dextrin of cyclomaltodextrin glucanotransferase, and subjected to an enzymatic reaction at pH 8.5 or higher and at 55° C. for 40 hours under anaerobic- and stirring-conditions. HPLC analysis of the reaction solution revealed that about 50% quercetin was converted into an α-glycosyl quercetin.

The reaction solution was neutralized, heated to inactivate the remaining enzyme and filtered. Similarly as in Example A-1, the filtrate was in the usual manner purified, concentrated and spray-dried to obtain a powdery mixture of a flavonoid and an α-glycosyl quercetin containing an α-glucosyl saccharide in the yield of about 85% against the weight of the material, d.s.b.

The product can be advantageously used in combination with other materials in food products, cigarettes, tobaccos, agents for susceptive diseases, cosmetics and plastics, as a vitamin p-enriched agent with an improved water-solubility, as well as a highly-safe and natural yellow-color-imparting agent, antioxidant, deodorant, stabilizer, quality-improving agent, antiseptic, prophylactic agents, therapeutic agents and ultraviolet-absorbing agents.

EXAMPLE A-4

Mixture of α-glycosyl Quercetin and Flavonoid

A filtrate of a post-reaction solution, prepared in accordance with the method in Example A-3, was fed at a flow rate of SV 1.5 to a column packed with "Amberlite XAD-7", a synthetic macroporous resin commercialized by Rohm & Haas Company, Philadelphia, USA.

As a result, an α-glycosyl quercetin and intact flavonoids in the filtrate adsorbed on the resin, while dextrin, oligosaccharides and salts were eluted from the column without adsorbing on the resin.

The column was first washed with water, then fed with 50 v/v % methanol to elute the α-glycosyl quercetin and intact flavonoids. The effluent was concentrated and pulverized to obtain a powdery mixture of the α-glycosyl quercetin and flavonoids in the yield of about 55% against the weight of the material flavonoid mixture, d.s.b.

The product can be advantageously used in combination with other materials in food products, cigarettes, tobaccos, agents for susceptive diseases, cosmetics and plastics, as a vitamin p-enriched agent with an improved water-solubility, as well as a highly-safe and natural yellow-color-imparting agent, antioxidant, deodorant, stabilizer, quality-improving agent, antiseptic, prophylactic agents, therapeutic agents and ultraviolet-absorbing agents.

EXAMPLE A-5

α-Glycosyl Quercetin

EXAMPLE A-5(1)

Preparation of α-Glucosidase Specimen

A liquid culture medium consisting of 4 w/v % maltose, 0.1 w/v % potassium hydrogenphosphate, 0.1 w/v % ammonium nitrate, 0.05 w/v % magnesium sulfate, 0.05 w/v % potassium chloride, 0.2 w/v % polypeptone, 1 w/v % calcium carbonate (presterilized by heating and antiseptically added to the culture medium at a seeding time) and water was prepared, and 500 hundred parts by weight of the culture medium was inoculated with a seed culture of *Mucor javanicus* IFO 4570 and incubated at 30° C. for 44 hours under shaking conditions. After completion of the cultivation, the resultant mycelia were recovered and 48 parts by weight of the wet mycelia was added with 50 parts by weight of 4M urea solution which had been prepared by dissolving urea in 0.5M phosphate buffer (pH 5.3), and the mixture was allowed to stand at 30° C. for 40 hours and centrifuged. The resultant supernatant was dialyzed overnight against flowing water, added with ammonium sulfate to give a saturation degree of 0.9, and allowed to stand at 4° C. overnight, and the salted-out sediment was recovered by filtration, suspended and dissolved in 50 parts by weight of 0.01M acetate buffer (pH 5.3) and centrifuged, followed by recoverying the resultant supernatant, an α-glucosidase specimen.

EXAMPLE A-5(2)

Preparation of α-Glycosyl Quercetin

Three parts by weight of quercetin and 20 parts by weight of dextrin (DE 30) were added to 500 parts by weight of 20 v/v % aqueous ethanol solution, and the suspension was adjusted to pH 9.0, dissolved by heating under an anaerobic condition, cooled to 55° C., immediately added with 15 parts by weight of an α-glucosidase specimen prepared by the method in Example A-5(1), and subjected to an enzymatic reaction at 50° C. and at pH 8.5 or higher for 40 hours under a stirring condition. HPLC analysis of the reaction solution revealed that about 30% quercetin was converted into an α-glycosyl quercetin.

Similarly as in Example A-3, the reaction solution was purified, concentrated and pulverized to obtain an α-glycosyl quercetin powder containing an α-glucosyl saccharide in the yield of about 80%.

Similarly as the product in Example A-3, the product can be advantageously used in combination with other materials in a variety of products as a vitamin P-enriched agent with an improved water-solubility, as well as a highly-safe and natural yellow-color-imparting agent, antioxidant, stabilizer, quality-improving agent, prophylactic agent, therapeutic agent, and ultraviolet-absorbing agent.

EXAMPLE B-1

Hard Candy

One thousand and five hundred parts by weight of "MABIT®", a hydrogenated maltose syrup commercialized by Hayashibara Co., Ltd, Okayarea, Japan, was concentrated in vacuo up to give a moisture content of about 2% or lower, and admixed with an adequate amount of citric acid and one part by weight of a powdery mixture of an α-glycosyl quercetin and a flavonoid prepared by the method in Example A-4. The resultant mixture was in the usual manner molded and packed into a hard candy.

The product is a relatively-low caloric vitamin p-enriched hard candy having a relatively-low dental-carries inducibility.

EXAMPLE B-2 "Fuki-no-mizu-ni" (boiled big rhuharbs)

Fresh bog rhuharbs were pared, cut into short sticks, soaked in a diluted salt solution for hours, and boiled down in a solution containing a green-coloring agent, which had been prepared by mixing food blue No.1 (brilliant blue FCF)

and an α-glycosyl quercetin syrup prepared by the method in Example A-1, to obtain the captioned product having a brilliant blue.

The product having a natural taste is advantageously used as a material for Japanese-style foods.

EXAMPLE B-3

"Gyuhi" (starch paste)

To one part by weight of glutinous rice starch was added 1.2 parts by weight of water, and the mixture was gelatinized by heating while admixing it with 1.5 parts by weight of sugar, 0.7 parts by weight of "SUNMALT®", a crystalline β-maltose product commercialized by Hayashibara Co., Ltd., Okayama, Japan, 0.3 parts by weight of partial starch hydrolysate, and 0.02 parts by weight of an α-glycosyl quercetin powder prepared by the method in Example A-5. Thereafter, the resultant mixture was in an usual manner formed and packed to obtain the captioned product.

The product having a natural taste is a Japanese-style confectionery like a "kibi-dango" (millet dumpling).

EXAMPLE B-4

Mixed Sweetener

One hundred parts by weight of honey, 50 parts by weight of isomerized sugar, one part by weight of "αG sweet", an α-glycosyl stevioside product commercialized by Toyo Sugar Refining Co., Ltd., Tokyo, Japan, and 0.02 parts by weight of a powdery mixture of an α-glycosyl quercetin and a flavonoid prepared by the method in Example A-4.

The product, a vitamin P-enriched sweetener, has a satisfactory taste-quality and about 2-fold higher sweetening power than sucrose, and these render the product advantageously useful as a health food.

EXAMPLE B-5

Cream Filling

One thousand and two hundred parts by weight of "FINE-TOSE®", a crystalline α-maltose powder commercialized by Hayashibara Co., Ltd., Okayama, Japan, 1,000 parts by weight of shortening, 50 parts by weight of cacao mass, 3 parts by weight of an α-glycosyl quercetin powder prepared by the method in Example A-2, and one part by weight of lecithin were mixed in an usual manner to obtain a cream.

The product is a vitamin P-enriched cream filling having a chocolate-like taste, as well as a satisfactory biting-property and meltability.

EXAMPLE B-6

Tablet

Ten parts by weight of L-ascorbic acid was added with 19 parts by weight of crystalline α-maltose, 10 parts by weight of a powdery mixture of an α-glycosyl quercetin and a flavonoid prepared by the method in Example A-3, and one part by weight of "αG rutin", an α-glycosyl rutin product commercialized by Toyo Sugar Refining Co., Ltd., Tokyo, Japan, and the mixture was mixed to homogeneity and tabletted with a 20 R punch, diameter of 12 mm, to obtain a tablet.

The product is an easily swallowable mixed-vitamin-agent containing L-ascorbic acid, α-glycosyl rutin and a mixture of an α-glycosyl quercetin and a flavonoid wherein the L-ascorbic acid is satisfiably stabilized.

EXAMPLE B-7

Capsule

Ten parts by weight of calcium acetate monohydrate, 50 parts by weight of magnesium L-lactate trihydrate, 57 parts by weight of maltose, 20 parts by weight of a powdery mixture of an α-glycosyl quercetin and a flavonoid prepared by the method in Example A-4, and 12 parts by weight of a γ-cyclodextrin inclusion complex containing 20% eicosapentaenoic acid were mixed to homogeneity, subjected to a granulator and encapsulated in gelatin in an usual manner to obtain capsules, 150 mg each.

The product can be advantageously used as a blood-cholesterol-lowering agent, immunoactivator, skin-refining agent, prophylactic or therapeutic agent for susceptive disease, and food product for promoting health.

EXAMPLE B-8

Ointment

One part by weight of sodium acetate trihydrate and 4 parts by weight of DL-calcium lactate were mixed to homogeneity with 10 parts by weight of glycerine, and the mixture was added with 50 parts by weight of petrolatum, 10 parts by weight of vegetable wax, 10 parts by weight of lanolin, 14.5 parts by weight of sesame oil, one part by weight of a powdery mixture of an α-glycosyl quercetin and a flavonoid prepared by the method in Example A-4, and 0.5 parts by weight of peppermint oil, and mixed to homogeneity to obtain the captioned product.

The product can be advantageously used as a sun-screening, skin-refining agent, skin-whitening agent and promotor for healing injury and burn.

EXAMPLE B-9

Injection

An α-glycosyl quercetin powder prepared by the method in Example A-2 was dissolved in water and sterilely filtered in an usual manner to obtain a pyrogen-free solution which was then distributed to 20 ml-glass-vials to give an α-glycosyl quercetin content of 10 mg, freeze-dried and sealed to obtain an injection.

The product is intramuscularly or intravenously administrable to a recipient alone or in combination with other vitamins and minerals. The product does not require a cold storage and it readily dissolves in physiological saline when in use.

EXAMPLE B-10

Injection

Six parts by weight of sodium chloride, 0.3 parts by weight of potassium chloride, 0.2 parts by weight of calcium chloride, 3.1 parts by weight of sodium lactate, 45 parts by weight of maltose, and one part by weight of an α-glucosyl quercetin powder prepared by the method in Example A-2 were dissolved in 1,000 parts by weight of water. The resultant solution was sterilely filtered in an usual manner to obtain a pyrogen-free solution, and 250 ml aliquots thereof were distributed to plastic containers to obtain the captioned product.

The product, which is an injection for supplementing vitamin P, energy and minerals, is advantageously useful for promoting the treatment and the recovery of health during or after diseases.

EXAMPLE B-11

Intubation Nutrition

A composition consisting of 20 parts by weight of crystalline maltose, 1.1 parts by weight of glycine, 0.18 parts by weight of sodium glutamate, 1.2 parts by weight of salt, one part by weight of citric acid, 0.4 parts by weight of calcium lactate, 0.1 part by weight of magnesium carbonate, 0.01 part by weight of a powdery mixture of an α-glycosyl quercetin and a flavonoid prepared by the method in Example A-3, 0.01 part by weight of thiamine, and 0.01 part by weight of riboflavin was prepared. Twenty-four g aliquots of the composition were injected to laminated aluminum-bags and heat sealed to obtain the captioned product.

The product can be advantageously used as an oral or parenteral intubation nutrition by dissolving one bag of the product in about 300–500 ml water and administering the solution to the nasal cavity, stomach or intestine.

EXAMPLE 12

Bath Salts

A mixture consisting of 21 parts by weight of DL-sodium lactate, 8 parts by weight of sodium pyruvate, 5 parts by weight of an α-glycosyl quercetin syrup prepared by the method in Example A-1, and 40 parts by weight of ethanol was mixed with 26 parts by weight of refined water and adequate amounts of a color-imparting agent and a flavor-imparting agent to obtain the captioned product.

The product can be suitably used as a skin-refining agent and skin-whitening agent and used by diluting it 100–10,000-fold with hot water in a bathtub, when in use. The product can be advantageously used by diluting it similarly as above with a cleansing liquid or lotion, prior to use.

EXAMPLE B-13

Milky Lotion

One half part by weight of polyoxyethylene behenyl ether, one part by weight of polyoxyethylene sorbitol tetraoleate, one part by weight of oil-soluble glyceryl monosterate, 0.5 parts by weight of pyruvic acid, 0.5 parts by weight of behenyl alcohol, one part by weight of avocado oil, one part by weight of an α-glycosyl quercetin syrup prepared by the method in Example A-1, and adequate amounts of an antiseptic and vitamin E were dissolved by heating in an usual manner, and the resultant solution was added with one part by weight of L-sodium lactate, 5 parts by weight of 1,3-butylene glycol, 0.1 part by weight of carboxy vinylpolymer and 85.3 parts by weight of refined water. The resultant mixture was emulsified by a homogenizer, added with an adequate amount of a flavoring agent and mixed while stirring to obtain a milky lotion.

The product can be advantageously used as a sun-screening, skin-refining agent and skin-whitening agent.

EXAMPLE B-14

Cream

Two parts by weight of polyoxyethylene glycol monostearate, 5 parts by weight of self-emulsifying glycerine monostearate, 2 parts by weight of a powdery mixture of an α-glycosyl quercetin and a flavonoid prepared by the method in Example A-3, one part by weight of liquid paraffin, 10 parts by weight of glyceryl trioctanate and an adequate amount of an antiseptic were dissolved by heating in an usual manner, and the resultant solution was added with 2 parts by weight of L-lactic acid, 5 parts by weight of 1,3-butylene glycol and 66 parts by weight of refined water. The resultant mixture was emulsified by a homogenizer, added with an adequate amount of a flavoring agent and mixed while stirring to obtain a cream.

The product can be advantageously used as a sun-screening, skin-refining agent and skin-whitening agent.

As described above, the present invention has the following advantageous features: (i) An α-glycosyl quercetin is readily formed by a biochemical technique which contains a step of subjecting a solution containing quercetin and an α-glucosyl saccharide to the action of a saccharide-transferring enzyme; (ii) the α-glycosyl quercetin diminishes the drawback of intact quercetin, i.e. intact quercetin is substantially not soluble or insoluble in water; and (iii) the α-glycosyl quercetin exerts a yellow-color-imparting ability as intact quercetin and it is readily hydrolyzed in vivo into quercetin and D-glucose to exert the inherent physiological activity of quercetin without fear of causing side effects.

Thus, the α-glycosyl quercetin according to the present invention can be advantageously used as a highly-safe and natural vitamin P-enriched agent, yellow-color-imparting agent, antioxidant, deodorant, stabilizer, quality-improving agent, prophylactic agent, therapeutic agent, and ultraviolet-absorbing agent, and deterioration-preventing agent, in combination with other materials in food products, cigarettes, tobaccos, feeds, pet foods, agents for susceptive diseases, plastics and cosmetics such as skin-refining agents and skin-whitening agents.

Accordingly, the establishment of the present industrial-scale preparation of an α-glycosyl quercetin and its uses has a great significance in the fields of food products, cosmetics, pharmaceuticals and plastics.

While there has been described what is at present considered to be the preferred embodiments of the invention, it will be understood the various modifications may be made therein, and it is intended to cover in the appended claims all such modifications as fall within the true spirits and scope of the invention.

We claim:

1. A process for preparing α-glycosyl quercetin consisting of one molar quercetin and at least equimolar D-glucose residues which are bound to said quercetin by an α-bond, said α-glycosyl quercetin capable of being hydrolyzed by α-glucosidase E.C. 3.2.1.20 into quercetin and D-glucose residue but not hydrolyzed by β-glucosidase, said process comprising:

(a) providing a solution of quercetin and an α-glucosyl saccharide;

(b) transferring D-glucose residue from said α-glucosyl saccharide to said quercetin in said solution by a saccharide-transfering enzyme in an amount which completes the transference within a period of from about 5–80 hours, said enzyme being a member selected from the group consisting of α-glucosidase, cyclomaltrodextrin glucanotransferase, and α-amylase; and (c) purifying the resultant solution to obtain said α-glycosyl quercetin.

2. The process of claim 1, wherein said α-glucosyl saccharide is selected from the group consisting of amylose, dextrins, cyclodextrins, maltooligosaccharides, and partial starch hydrolysates.

3. The process of claim 1, wherein the concentration of said quercetin in the step (a) is at least 0.01 w/v %.

4. The process of claim 1, wherein the concentration of said α-glucosyl saccharide in the step (a) is 0.5–100-fold of that of said quercetin.

5. The process of claim 1, wherein in step (c) purification is effected using a macroporous synthetic resin.

6. An α-glycosyl quercetin prepared by the process of claim 1 which consists of one mole of quercetin and at least two moles of D-glucose residues which bind to quercetin via an α-bond, said α-glycosyl quercetin is hydrolyzed by α-glucosidase into quercetin and D-glucose residues but said α-glycosyl quercetin is not hydrolyzed by β-glucosidase.

7. A composition which comprises a carrier and an α-glycosyl quercetin consisting of two or more of D-glucose residues which are bound to quercetin by an α-bond, said α-glycosyl quercetin being hydrolyzed by α-glycosyl glucosidase EC 3.2.1.20 into quercetin and D-glucose residues.

8. The composition of claim 7 wherein said α-glycosyl quercetin is prepared by a process comprising:

(a) providing a solution of quercetin and an α—glucosyl saccharide;

(b) transferring two or more D-glucose residues from said α-glucosyl saccharide to said quercetin in said solution by a saccharide-transferring enzyme in an mount of which completes the transference within a period of from about 5–80 hours, said enzyme being selected from the group consisting of α-glucosidase, cyclomaltodextrin glucanotransferase, and α-amylase; and (c) purifying the resultant solution to obtain said α-glycosyl quercetin.

9. The composition of claim 8, wherein said α-glycosyl saccharide is selected from the group consisting of amylose, dextrins, cyclodextrins, maltooligosaccharides, and partial starch hydrolysates.

10. The composition of claim 8, wherein the concentration of said quercetin in step (a) is at least 0.01 w/v %.

11. The composition of claim 8 wherein the concentration of said α-glucosyl saccharide in step (a) is 0.5 to 100-fold of that of said quercetin.

12. The composition of claim 8 wherein in step (c) purification is effected using a macroporous synthetic resin.

* * * * *